United States Patent [19]

Weaver

[11] 4,000,743
[45] Jan. 4, 1977

[54] UTERINE ANTEVERTER

[76] Inventor: Kenneth Weaver, 1511 N. Main, Waynesville, N.C. 28786

[22] Filed: July 9, 1975

[21] Appl. No.: 594,203

[52] U.S. Cl. ............................ 128/303 R; 128/348; 128/DIG. 26

[51] Int. Cl.² ................. A61B 17/42; A61M 25/02

[58] Field of Search .......... 128/239, 240, 241, 245, 128/303 R, 321, 323, 324, 345, 348, 361; 285/184

[56] References Cited

UNITED STATES PATENTS

| 639,576 | 12/1899 | Hurlbut | 128/239 |
|---|---|---|---|
| 1,314,855 | 9/1919 | Carpenter | 128/240 |
| 1,559,737 | 11/1925 | Bock | 128/345 |
| 2,278,356 | 3/1942 | Livingston | 285/184 X |
| 2,482,622 | 9/1949 | Kahn | 128/321 X |
| 3,796,211 | 3/1974 | Kohl | 128/348 X |
| 3,809,091 | 5/1974 | Shute | 128/303 R |
| 3,877,433 | 4/1975 | Librach | 128/303 R |

*Primary Examiner*—Channing L. Pace
*Attorney, Agent, or Firm*—Bell, Seltzer, Park & Gibson

[57] ABSTRACT

An apparatus for moving a retroverted uterus to an anterior position to facilitate visualization of the uterus during laparoscopic procedures and the like. The apparatus comprises an elongate rod having an arcuately curved manipulating arm pivotally mounted at the forward end of the rod. The arm is adapted to be inserted into the uterine cavity, and may then be manually pivoted into an upright position to reposition the uterus by manipulating a lever arm carried at the rearward end of the rod. The apparatus is adapted to be releasably attached to a standard tenaculum so as to become self-retained after the arm is inserted in the uterine cavity, and a latch is provided for releasably locking the arm in the repositioned setting.

9 Claims, 6 Drawing Figures

U.S. Patent  Jan. 4, 1977  Sheet 1 of 2  4,000,743
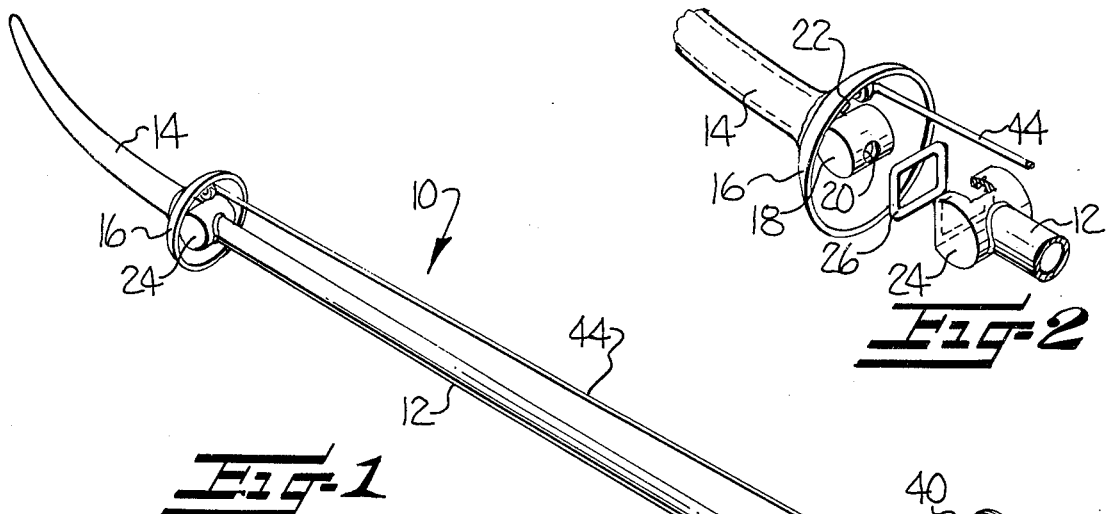
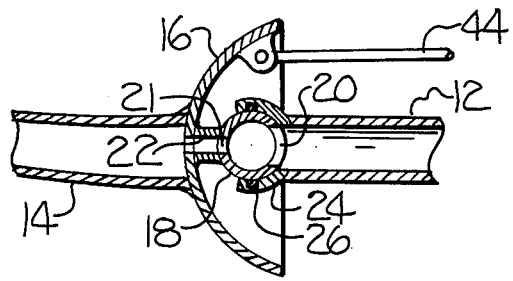
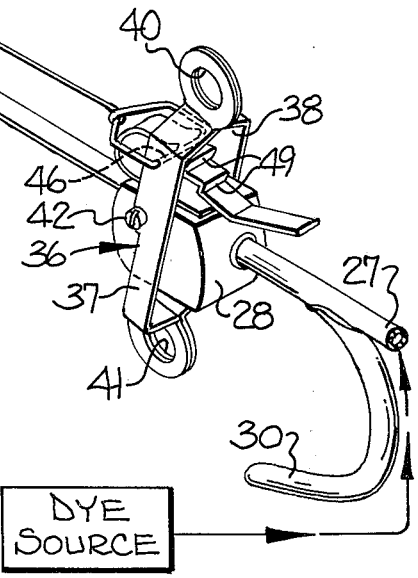
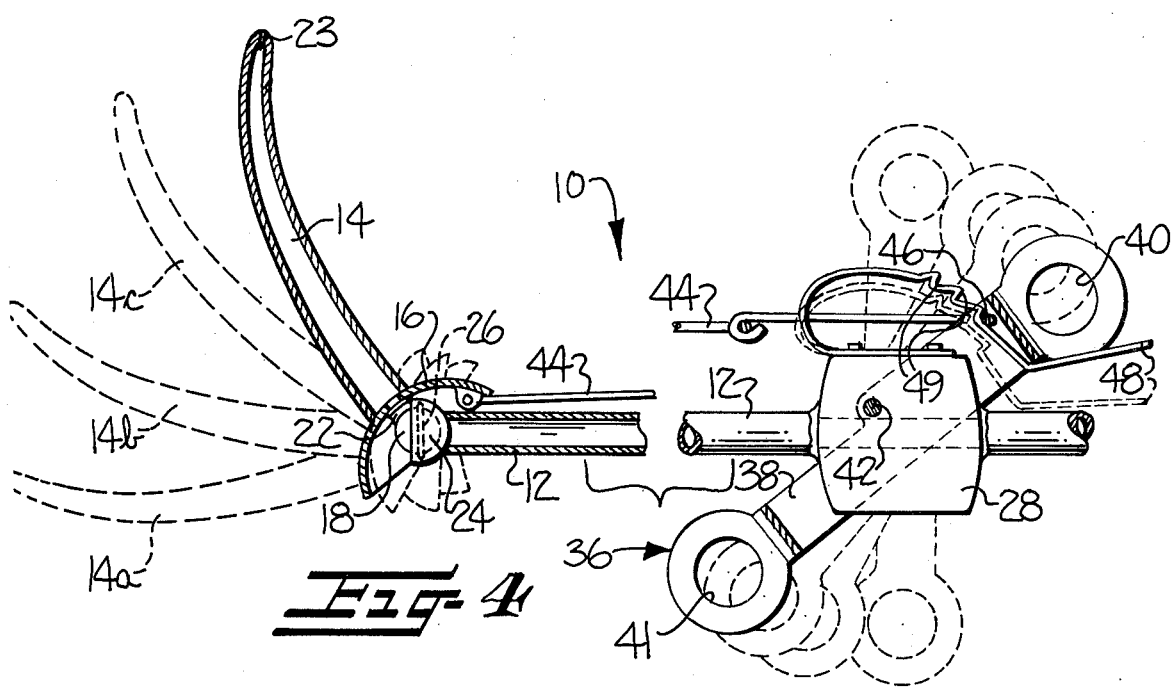

UTERINE ANTEVERTER

The present invention relates to an apparatus adapted to move a retroverted uterus into an anterior position, and to retain the uterus in such position, during various operations which involve an examination of the interior of the abdomen or peritoneal cavity.

In the performance of a laparoscopic procedure, a small incision is made in the wall of the abdomen, and a laparoscope is inserted therethrough to permit visualization of the peritoneal cavity. This procedure is commonly performed to permit visualization of the uterus for the purpose of sterilization, by either coagulation or placing metallic clips on the fallopian tubes, or for the purpose of investigating tubal patency in cases of infertility. In addition, the procedure is commonly used in a uterine suspension wherein the ligaments of the uterus are attached to the anterior fascial sheath of the abdominal wall.

A common problem associated with the above procedure resides in the fact that the uterus of many women, and particularly women who have borne children, is in an abnormal or retroverted position and extends downwardly into the peritoneal cavity. When so located, it is extremely difficult for the physician to visualize the uterus and fallopian tubes, and the danger of an improper or incomplete procedure, such as incomplete coagulation of the fallopian tubes during a sterilization procedure, is increased.

Several prior devices for positioning the uterus have been proposed for various purposes, but such devices are not suitable for use in the above laparoscopic procedure. For example, the U.S. Pat. No. to Chisholm, 424,178, represents an early uterine repositor for use during examination of the uterus, and which comprises a scissors-like lever for pivoting a forward arm which is adapted to be positioned in the uterine cavity. The more recent patent to Shute, U.S. Pat. No. 3,809,091 shows a curved instrument which is designed to be rotated to retrovert the uterus. However, there is no provision in either the Chisholm or Shute devices for retaining the instrument in its repositioned setting, which is an important requirement in the performance of the above laparscopic procedure. More particularly, once the abdominal incision is made in a laparoscopic procedure, the physician is unable to return to the vaginal canal to reset or correct the positioning of the uterus since the vaginal canal is not sterile. Accordingly, it is important that the physician be able to properly position the uterus in its anterior position prior to "scrubbing", and that the instrument be able to retain the proper position of the uterus without further attention from the physician during the entire course of the procedure.

It has recently become common to employ a conventional cannula having a non-movable tip in association with a standard tenaculum in an attempt to position the uterus during laparscopic procedures. In such prior practice, the tip of the cannula is inserted in the uterine cavity, and then the cannula is attached in the conventional manner to a tenaculum which has been affixed to the cervix, to thereby retain the tip of the cannula within the uterine cavity. This arrangement is unsatisfactory however, since the cannula is unable to give anterior flexion, which is important in aiding visualization of the uterus through the laparscope.

Accordingly, it is an object of the present invention to provide an apparatus for positioning a retroverted uterus into an anterior position to thereby facilitate visualization during various laparscopic procedures.

It is another object of the present invention to provide an apparatus of the described type which is adapted to be attached to a standard tenaculum so as to be self-retained within the uterus, and which may further be locked in the desired anterior setting, to thereby eliminate the need for further attention from the physician after once being set.

It is another object of the present invention to provide an apparatus of the described type which is adapted to minimize trauma to the uterus by employing multiple points of contact and stress.

It is still another object of the present invention to provide an apparatus of the described type which is readily adapted to be made hollow such that the apparatus may be employed for injecting a dye into the uterus as part of an infertility investigation or the like.

These and other objects and advantages of the present invention are achieved in the embodiment illustrated herein by the provision of an apparatus which comprises an elongate rod having a manipulating arm pivotally carried at the forward end thereof. The arm is curved to approximate the natural curvature of the uterine cavity, and has a length sufficient to extend a substantial distance thereinto. A cross bar is pivotally carried at the rear end of the rod, and the cross bar is operatively connected to the forward arm such that the arm may be pivoted between a first position substantially coaxial with the rod and a second generally upright position. The cross bar in turn carries a latching member which is adapted to engage a cooperating catch carried by the rod, so as to releasably lock the arm in its upright position.

The cross bar may further carry an open ring which is adapted to receive the latch portion of a tenaculum therethrough, such that the apparatus may be retained in an operative position within the uterine cavity by attaching the tenaculum to the anterior or posterior lip of the cervix, and attaching the apparatus to the tenaculum.

Some of the objects and advantages of the invention having been set forth, other objects and advantages will appear, when taken in conjunction with the accompanying drawings, in which:

FIG. 1 is a perspective view of an apparatus embodying the features of the present invention;

FIG. 2 is a fragmentary exploded perspective view of the pivotal interconnection between the rod and forward arm of the apparatus shown in FIG. 1;

FIG. 3 is a fragmentary sectional view of the pivotal interconnection between the rod and forward arm;

FIG. 4 is a side elevation view of the apparatus, partly sectioned, and illustrating the manner in which the forward arm may be pivoted by the physician;

Figure 5:
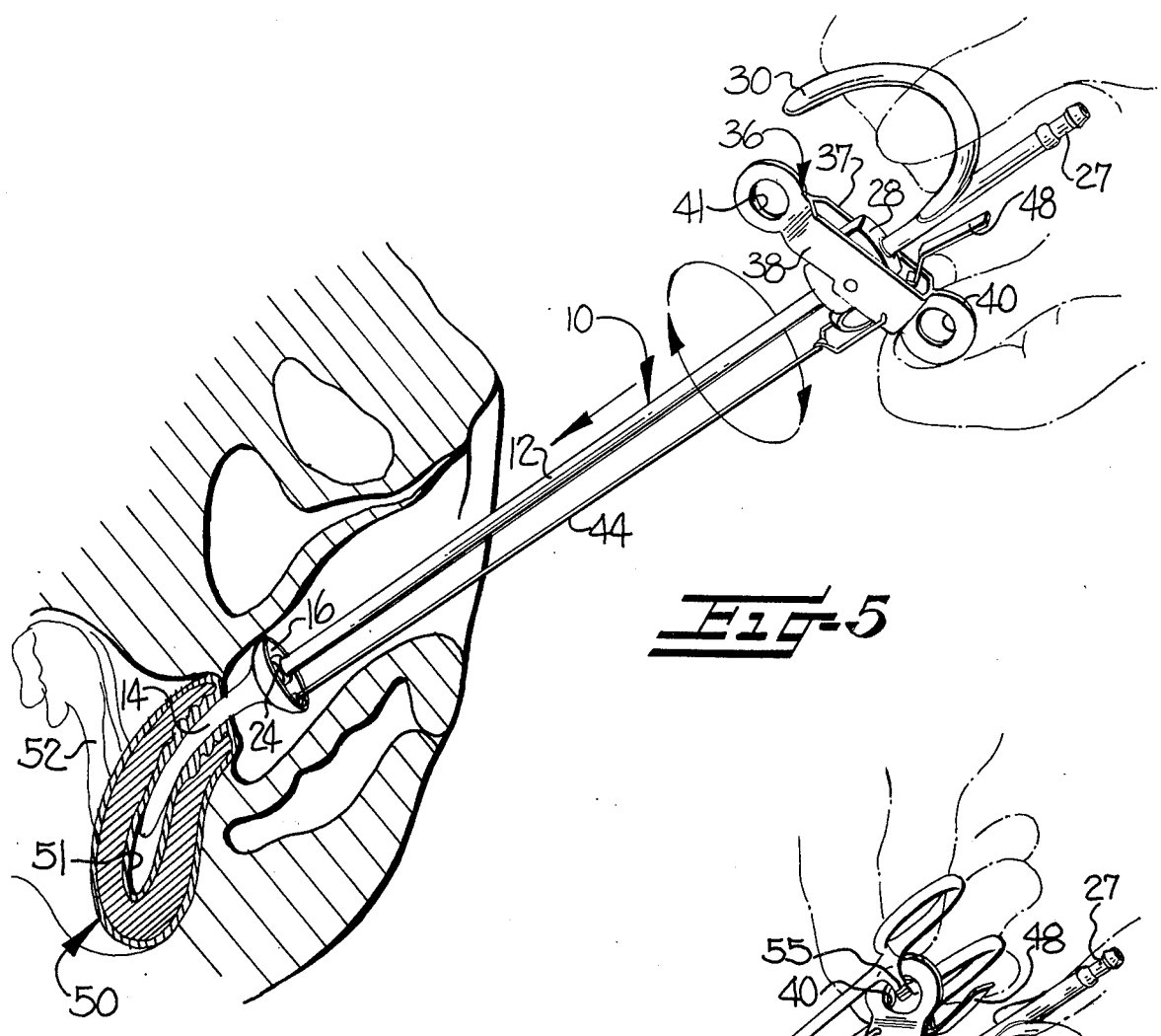
FIG. 5 is a diagramatic view of the apparatus in position within the vagina and uterus, with the uterus being shown in its abnormal or retroverted position.
Figure 6:
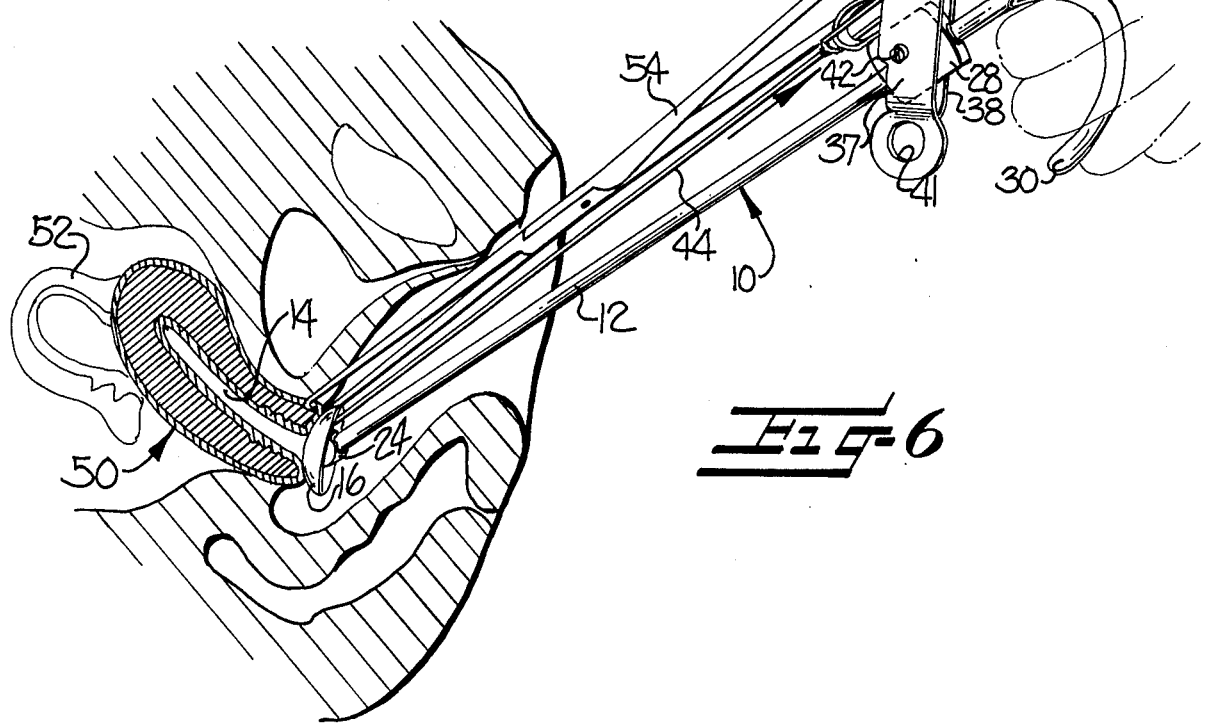
FIG. 6 is a diagrammatic view similar to FIG. 5 and illustrating the uterus in its normal or anterior position.

Referring more specifically to the drawings, an apparatus embodying the features of the present invention is illustrated generally at 10. The apparatus comprises an elongate rod 12 having a length of between about 7 to 8 inches, and a forward manipulating arm 14 pivotally mounted at the forward end of the rod. The arm 14 has a length sufficient to extend a substantial distance into the uterine cavity as seen in FIGS. 5 and 6, and it is arcuately curved along its length to approximate the natural curvature of the uterine cavity. In this regard, the rear end portion of the arm 14 coaxially carries an arcuately curved shield 16 to limit the distance which the arm may be inserted into the uterine cavity as hereinafter futher explained.

In the illustrated embodiment, the rod 12 and arm 14 are both fabricated from a tubular metallic material and the means for pivotally attaching the arm to the rod includes a passageway extending therebetween. More particularly, the pivotal interconnection includes a hollow cylindrical member 18 fixedly mounted to the rear end of the arm 14, the member 18 extending generally transversely to the axis of the arm. The cylindrical member 18 has closed opposite ends, and further includes a pair of aligned apertures 20 and 21 which communicate through the tubular attaching member 22 to the interior or bore of the arm 14. Also, the forward end of the arm includes an exit opening 23 for the purposes set forth below.

The forward end of the rod 12 includes a mating receptable 24 which is adapted to substantially receive the cylindrical member 18 of the arm so as to permit relative pivotal movement about a transverse pivotal axis and in a vertical plane as seen in FIGS. 1 and 4. The receptacle 24 communicates with the bore of the tubular rod 12, such that in its assembled configuration, the bore of the rod 12 communicates with the bore of the tubular arm, note FIG. 3. This assembled configuration may be maintained by crimping the edges of the receptacle 24 about the cylindrical member 18, and also, a pivot pin (not shown) may be positioned to extend along the pivotal axis and throught the receptacle 24 and cylindrical member 18 to more positively interconnect the two members. A sealing ring 26 may also be interposed between the receptacle and cylindrical member to sealably interconnect the two members.

The rear end of the rod 12 mounts a nipple, such as a conventional Luer connector 27 for the purposes set forth below and a mounting block 28 is fixedly mounted to the rod immediately adjacent the rear end. also, a curved handle 30 extends rearwardly and downwardly from the rear end of the rod to facilitate manual gripping thereof by the physician, note FIGS. 5 and 6. The handle 30 may be fabricated from a tubular material similar to that of the rod 12, but the bore thereof preferably does not communicate with the bore of the rod.

The forward manipulating arm 14 is pivotally controlled by an arrangement which includes a cross bar 36 carried by the mounting block 28 of the rod. More particularly, the cross bar 36 includes parallel side legs 37, 38 which straddle the block 28 and which extend laterally in opposite directions from the rod 12 in a generally vertical plane as seen in FIG. 1. The upper ends of the legs 37, 38 are directed inwardly and are joined to define a first open ring 40 positioned above the mounting block 28, and the lower ends of the legs are similarly joined to define a second open ring 41 below the mounting block. The cross bar 36 is pivotally secured to the mounting block by means of a cross pin 42 which extends through the legs and mounting block to define a horizontal pivotal axis. Further, a rigid wire 44 is provided which has one end pivotally attached to the shield 16 and the other end pivotally attached to the upper portion of the legs 37, 38, such that the arm 14 may be selectively pivoted between a first position substantially coaxial with the rod, and a second generally upright position as seen in solid lines in FIG. 4. More particularly, the arm 14 is pivoted between a first coaxial position 14a as seen in FIG. 4, a pair of intermediate positions 14b and 14c, and a fully upright position as seen in solid lines.

To releasably lock the arm 14 in one of its intermediate, or its fully upright position, there is provided a locking arrangement which includes a transverse segment 46 of the wire which extends between the legs 37, 38 of the cross bar, and a spring biased catch 48 carried by the upper surface of the mounting block. The catch comprises a flexible spring steel member or the like, and includes a number of locking shoulders 49. The wire segment 46 thus acts as a latching member which is adapted to lock behind one of the shoulders 49 when the cross bar 36 and arm 14 are pivoted into one of the intermediate or fully upright positions. To release the inter-engagement, the physician merely presses downwardly on the catch 48 to separate the locking shoulders 49 from the wire segment 46, and permit the cross bar to pivot rearwardly.

The manner in which the apparatus 10 is utilized may be best described with reference to FIGS. 5 and 6. In this regard, it will be understood that the apparatus 10 is normally used in association with a conventional speculum, which has not been shown in the drawings for clarity of illustration.

Initially, the orientation of the uterus 50 is determined by the physician by a pelvic examination. As seen in FIG. 5, the uterus 50 is shown in the retroverted position, in which event the apparatus 10 is inverted so that the manipulating arm 14 may be inserted into the uterine cavity 51 with the curvature of the arm 14 substantially following the natural curvature of the cavity 51. In this regard, it will be noted that the shield 16 serves to limit the extent to which the arm 14 may be inserted into the cavity, and further serves to protect the cervix from contact with the pivotal interconnection between the rod 12 and arm 14.

After insertion, the apparatus 10 is rotated by the physician to lift the uterus slightly, and the forward arm 14 is then pivoted by pulling the upper portion of the cross bar 36 rearwardly. The latching member 46 freely slides downwardly over the shoulders 49 of the catch 48, and is automatically engaged by the most rearward shoulder. The uterus is thereby lifted to the desired anterior position as shown in FIG. 6 to lift and expose the fallopian tubes 52, and the arm 14 is automatically locked in its upright position by the catch 48.

To retain the apparatus and uterus in the desired position as seen in FIG. 6, a conventional tenaculum 54 is positioned to grip to anterior lip of the cervix, with the latching or toothed portion 55 of the tenaculum extending through the open ring 40. In this regard, tenacula of this type come in a variety of sizes and lengths, and one is chosen which will properly mate with the apparatus so that the latching portion 55 may be received through the open ring 40. Thus the ring 40 serves to releasably attach the apparatus 10 to the tenaculum, and thereby assures that the apparatus may be retained in its operative position within the uterine cavity 51. More particularly, the tenaculum 54 is attached to the anterior lip of the cervix, and the apparatus 10 is attached to the tenaculum 54, thereby precluding withdrawal of the apparatus from the uterine cavity. Since pivotal movement of the forward arm 14 is also precluded by the catch 48, the proper positioning of the uterus 50 is assured during the remaining portion of the operative procedure.

In order to further assure retention of the apparatus 10 and uterus in the desired position, a second tenaculum (not shown) may be attached to the posterior lip of the cervix, with the latching portion thereof extending through the lower open ring 41. In this case, two tenacula would concurrently engage the cervix, with each being releasably secured to the apparatus 10. Here again, the size of the second tenaculum will be chosen so as to properly mate with the lower open ring 41.

As noted above, certain procedures involve the injection of a dye into the uterine canal. The apparatus 10 of the present invention is adapted to perform this function, with the dye entering through the entry port at the connector 27, passing through the rod 12, and exiting through the exit port 23 at the remote free end of the arm 14.

As a further aspect of the present invention, it will be seen that the apparatus 10 is able to minimize trauma to the uterus by employing multiple points of contact and stress. In particular, the multiple actions of gripping the anterior lip of the cervix, gripping the posterior lip where a second tenaculum is employed, and applying pressure inside the uterine cavity by the arm 14, serve to reposition the uterus without significant trauma.

The apparatus 10 is preferably fabricated entirely from suitable metallic materials, such as stainless steel, to permit the entire apparatus to be easily sterilized by autoclaving.

In the drawings and specification, there has been set forth a preferred embodiment of the invention, and although specific terms are employed, they are used in a generic and descriptive sense only and not for purposes of limitation.

That which is claimed is:

1. An apparatus for moving a retroverted uterus to an anterior position to facilitate visualization of the uterus during a laparoscopic procedure or the like, and characterized by the ability to be self-retained in its operative position so as to avoid the need for further attention from the physician during the course of the procedure, said apparatus comprising an elongate rod having a forward end and a rearward end, a manipulating arm having one end pivotally mounted immediately adjacent said forward end of said rod, said arm having a length sufficient to extend a substantial distance into the uterine cavity and including a shield coaxially disposed about said one end of said arm so as to lie closely adjacent the pivotal connection between said arm and rod to limit the distance which said arm may be inserted into the uterine cavity and to effectively preclude contact between the pivotal connection and the body of the patient during use, means carried at said rearward end of said rod and operatively connected to said arm for selectively pivoting said arm between a first position substantially coaxial with said rod and a second generally upright position which is angularly disposed with respect to said rod, means for releasably holding said arm in said upright position, and means for releasably attaching the apparatus to a tenaculum such that the apparatus may be retained in an operative position within the uterine cavity by attaching the tenaculum to the anterior or posterior lip of the uterus and attaching the apparatus to the tenaculum.

2. The apparatus as defined in claim 1 wherein said arm is curved along its length to approximate the natural curvature of the uterine cavity.

3. The apparatus as defined in claim 2 further comprising a handle disposed at said rearward end of said rod and extending in a generally transverse direction with respect to said rod to facilitate manual gripping thereof by the physician.

4. The apparatus as defined in claim 3 wherein said means for pivoting said arm includes a cross bar pivotally carried by said rod adjacent said rearward end, and a rigid wire interconnecting said cross bar and said arm, said wire being attached to both said cross bar and said arm at a point spaced from the associated pivot point, such that pivotal movement of said cross bar results in a corresponding pivotal movement of said arm.

5. The apparatus as defined in claim 4 wherein said holding means comprises a latching member carried by said cross bar, and a cooperating catch carried by said rod and positioned so as to engage said latching member when said cross bar and arm are pivoted into said upright postion.

6. The apparatus as defined in claim 5 wherein said rod and arm are hollow, and further includes an entry port adjacent said rearward end of said rod, an exit port at the remote free end of said arm, and a communicating passageway across the pivotal interconnection of said rod and arm, whereby a fluid may be injected through said rod and arm and into the uterine cavity.

7. The apparatus as defined in claim 1 wherein said means for pivoting said arm includes a cross bar pivotally mounted to said rod adjacent said rearward end, and wherein said attaching means comprises an open ring carried by said cross bar, said ring being adapted to receive the latch portion of a tenaculum therethrough.

8. The apparatus as defined in claim 1 wherein said means for pivoting said arm includes a cross bar pivotally mounted to said rod adjacent said rearward end and extending laterally from said rod in opposite directions, and wherein said attaching means comprises a first open ring carried by said cross bar on one side of said rod and a second open ring carried by said cross bar, on the other side of said rod, said rings each being adapted to receive the latch portion of a tenaculum therethrough.

9. The apparatus as defined in claim 1 wherein said apparatus is fabricated from metal and is adapted to be sterilized by autoclaving.

* * * * *